(12) United States Patent
Laurent et al.

(10) Patent No.: US 7,582,069 B2
(45) Date of Patent: *Sep. 1, 2009

(54) METHOD AND DEVICE FOR THE DELIVERY OF A SUBSTANCE

(75) Inventors: Phillipe Laurent, Oullins (FR); John A. Mikszta, Durham, NC (US); Jason B. Alarcon, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/942,019

(22) Filed: Nov. 19, 2007

(65) Prior Publication Data

US 2008/0065005 A1     Mar. 13, 2008

Related U.S. Application Data

(63) Continuation of application No. 10/925,670, filed on Aug. 25, 2004, now Pat. No. 7,316,665.

(51) Int. Cl.
*A61N 1/30*        (2006.01)
(52) U.S. Cl. ...................................................... 604/19
(58) Field of Classification Search ............. 604/19, 604/46, 47, 48, 22, 20, 272, 304, 307, 890.1, 604/174, 500, 289–290, 501; 424/447, 449
See application file for complete search history.

(56) References Cited

U.S. PATENT DOCUMENTS

| | | | | | |
|---|---|---|---|---|---|
| 1,920,808 | A | * | 8/1933 | Sander | 128/888 |
| 3,918,449 | A | * | 11/1975 | Pistor | 604/47 |
| 5,983,136 | A | * | 11/1999 | Kamen | 604/21 |
| 7,316,665 | B2 | * | 1/2008 | Laurent et al. | 604/46 |

* cited by examiner

*Primary Examiner*—Manuel A Mendez
(74) *Attorney, Agent, or Firm*—Robert E. West (57) ABSTRACT

An abrasion device and method for delivery of substances into the skin using a microabrader for delivering a substance into the skin are disclosed. An abrasion device with a cover is also disclosed. Such devices and methods can be effectively used to deliver bioactive substances into skin.

20 Claims, 6 Drawing Sheets

METHOD AND DEVICE FOR THE DELIVERY OF A SUBSTANCE

CROSS REFERENCE TO RELATED APPLICATIONS

This application is a continuation of U.S. Ser. No. 10/925,670 filed Aug. 25, 2004.

FIELD OF THE INVENTION

The present invention relates to a method and device for abrading the skin.

BACKGROUND OF THE INVENTION

Delivery of substances to the body through the skin has typically been invasive, involving needles and syringes to facilitate intradermal (ID), intramuscular (IM) or subcutaneous (SC) injection. These methods may be painful for the subject, require the skills of a trained practitioner and often produce bleeding. There have been efforts to overcome these disadvantages by use of devices, which abrade the stratum corneum, the thin external layer of keratinized cells about 10-20 µm thick. The bioactive substance is delivered to the exposed viable epidermis.

This technique avoids the nerve net and deposits the bioactive substance in close proximity to blood vessels and lymphatics for absorption and delivery of the substance throughout the body.

For topical delivery of vaccines, the epidermis itself is a particularly desirable target as it is rich in antigen presenting cells. In comparison, the dermal layer below the epidermis contains fewer antigen-presenting cells. Furthermore, the stratum corneum and epidermis do not contain nerves or blood vessels, so this method has the advantage of being essentially painless and blood-free while giving access to the skin layers capable of responding to the antigen.

A variety of devices and methods purport to disrupt the stratum corneum for the purpose of delivering substances to the body. For example, breach of the stratum corneum may be achieved by puncturing as taught in U.S. Pat. No. 5,679,647 to Carson, et al. This patent teaches that narrow diameter tines, such as those found on devices used for tuberculin skin tests and allergy tests, can be coated with polynucleotides or oligonucleotides and used for delivery of such materials into the skin. The method of using such devices involves puncturing the skin with the tines resulting in intracutaneous injection of the coated substance.

U.S. Pat. Nos. 5,003,987; 5,879,326; and 3,964,482 teach breaching the stratum corneum by cutting.

SUMMARY OF THE INVENTION

The present invention is directed to a method and device for abrading the skin, and particularly, the stratum corneum of the skin.

Substances to be delivered particularly include bioactive substances, including pharmaceutical agents, medicaments, vaccines and the like. Substances may be in solid or liquid form, depending on formulation and delivery method. They can be delivered, inter alia, in the form of dry powders, gels, solutions, suspensions, and creams. Suitable formulations are familiar to those of skill in the art. Particularly preferred medicaments for delivery by the methods of the invention include vaccines, allergens and gene therapeutic agents.

One aspect of the invention is directed to a method and device for preparing a delivery site on the skin to enhance the delivery of a pharmaceutical agent through the stratum corneum of the skin to a sufficient depth where the pharmaceutical agent can be absorbed and utilized by the body.

Dermal tissue represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, especially the epidermal Langerhan's cells (LC). Several gene therapeutic agents are designed for the treatment of skin disorders, skin diseases and skin cancer. In such cases, direct delivery of the therapeutic agent to the affected skin tissue is desirable. In addition, skin cells are an attractive target for gene therapeutic agents, of which the encoded protein or proteins are active at sites distant from the skin. In such cases, skin cells (e.g., keratinocytes) can function as "bioreactors" producing a therapeutic protein which can be rapidly absorbed into the systemic circulation via the papillary dermis. In other cases, direct access of the vaccine or therapeutic agent to the systemic circulation is desirable for the treatment of disorders distant from the skin. In such cases, systemic distribution can be accomplished through the papillary dermis.

Aspects of the present invention provides a method and microabrader device to abrade the skin in conjunction with the delivery of a bioactive substance, including but not limited to nucleic acids, amino acids, amino acid derivatives, peptides or polypeptides. It has been discovered that nucleic acids exhibit enhanced gene expression and produce an enhanced immune response to the expressed protein when they are delivered simultaneously with abrasion of the stratum corneum. Similarly, allergens delivered simultaneously with abrasion produce a more vigorous immune response than conventional allergen testing methods provide.

In one aspect of the present invention, a microabrader is provided for delivering a substance into the skin. Typically, the microabrader has a base with an abrading face, to which an abrading surface that is composed of an arrangement of microprotrusions that have at least one scraping edge. A handle attachment may or may not be present on the microabrader, to which a handle or other grasping device is attached, mounted, or integral with. By "abrading surface" is meant the surface that is presented to the skin during the process of abrasion, including microprotrusions, surface area between them and surrounding surface.

Other aspects of the present invention involve methods for delivering a substance to the skin comprising the movement of the microabrader device across a predetermined area of the skin to produce furrows of sufficient depth to allow the substance, which is administered prior to, simultaneously with, or following the abrasion of the skin, to be taken up by the predetermined skin layer. By means of a microabrader device, multiple passes of the device across the skin can result in progressively deeper furrows in the skin, thereby allowing delivery of a substance to a desired depth with in the skin. Another aspect of the invention is a method of using a covering for use in conjunction with the microabrader device. Another aspect of the invention is a method of using a skin covering for use in conjunction with the microabrader device prior to abrasion. Another aspect of the invention is a method of using a skin covering which defines a predetermined surface area for use in conjunction with the microabrader device prior to and during abrasion.

In accord with another aspect of the invention, a device is provided having a plurality of microneedles for penetrating the stratum corneum and an outer adhesive patch for adhesively attaching the apparatus to the skin of a patient is provided, which includes an active drug delivery means.

DESCRIPTION OF THE DRAWINGS

Embodiments of the invention are explained in greater detail by way of the drawings, where like numerals refer to like elements, and wherein.

DETAILED DESCRIPTION OF THE INVENTION

The present invention is directed to devices and to methods for abrading the stratum corneum to enhance the administering of a substance through the stratum corneum of the skin of a patient.

In certain applications, substances may be delivered using the microabraders and methods of the invention. These substances include Alpha-1 anti-trypsin, Anti-Angiogenesis agents, Antisense, butorphanol, Calcitonin and analogs, Ceredase, chemokines, chemoattractants, chemokinetic agents, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Luteinizing hormone, Luteinizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Receptor agonists and antagonists, Recombinant soluble receptors, scopolamine, Serotonin agonists and antagonists, Sildenafil, Terbutaline, Thrombolytics, Tissue plasminogen activators, TNFα, and TNFα antagonist, vaccines, with or without carriers/adjuvants, including prophylactic and therapeutic antigens (including but not limited to subunit protein, peptide and polysacchraride, polysaccharide conjugates, toxoids, genetic based vaccines, live attenuated, reassortant, inactivated, whole cells, viruses, bacteria, viral and bacterial vectors including but not limited to those derived from adenoviruses, retroviruses and alphaviruses) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne Japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhea, asthma, atherosclerosis, malaria, E-coli, Alzheimer's Disease, *H. Pylori, salmonella*, diabetes, cancer, herpes simplex, human papilloma and like other substances include all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

For certain applications, particularly desirable substances that can be delivered using the microabraders and methods of the invention include drugs, vaccines, cell-based therapeutics and prophylactics, nucleic acid derived entities and gene therapeutics, and the like used in the prevention, diagnosis, alleviation, treatment, or cure of disease.

The devices and methods of the present invention are particularly suitable for delivery of a broad range of vaccines made by a variety of methods, including live attenuated bacterial and viral vaccines, killed bacterial and viral vaccines, genetically engineered vaccines, peptide, polypeptide, protein and nucleic acid vaccines. Suitable vaccines include smallpox (e.g., live, viral, based on vaccinia virus strain), Japanese (mosquito borne) encephalitis (e.g., ChimeriVax™-JE); yellow fever (e.g., Arilvax®, live attenuated) Dengue (mosquito borne, e.g., ChimeriVax™-Dengue), West Nile encephalitis (e.g., ChimeriVax™-West Nile), Hepatitis C, typhoid (e.g., HolaVax-typhoid, live attenuated bacterial vaccine), enterotoxigenic E. Coli (traveler's diarrhea, e.g. HolaVax-ETEC), Campylobacter, *H. pylori, C. difficile* (active and passive vaccines), measles (e.g., AttenuVax™, Moraten™, Morbilvax™, Rimevax™, and Rouvax™).

As used herein, the term "abrade" refers to removing at least a portion of the stratum corneum to increase the permeability of the skin without causing excessive skin irritation or compromising the skin's barrier to infectious agents. The term "abrasion" as used herein refers to disruption of the outer layers of the skin, for example by scraping or rubbing, resulting in an area of disrupted stratum corneum. This is in contrast to "puncturing" which produces discrete holes through the stratum corneum with areas of undisrupted stratum corneum between the holes.

The microabrader of certain aspects of the invention is a device capable of abrading the skin to attain this result. In implementations of aspects of the instant invention, the device is capable of abrading the skin thereby penetrating the stratum corneum without piercing the stratum corneum. In one aspect of the invention, the microabrader also includes an effective amount of a substance to be delivered. This may be included, for example, in a reservoir that is an integral or detachable part of the microabrader, or may be coated on the delivery surface of the microabrader. By an "effective amount" of a substance is intended to mean an amount that will elicit a desired response in a subject, including, but not limited to, an immunostimulatory or immunomodulatory response in the case of an allergen or vaccine, or another therapeutic or diagnostic response.

As used herein, "penetrating" refers to entering the stratum corneum without passing completely through the stratum corneum and entering into the adjacent layers. This is not to say that that the stratum corneum cannot be completely penetrated to reveal the interface of the underlying layer of the skin. Piercing, on the other hand, refers to passing through the stratum corneum completely and entering into the adjacent layers below the stratum corneum.

In certain situations, the microabrader device of certain aspects of the invention is believed to have a unique immunological advantage in the delivery of vaccines with the potential of increasing the vaccine's clinical value. The penetration of the multiple microprotrusions into the stratum corneum is suggested as having an adjuvant-like stimulatory effect. The "penetration" response from the multiple microprotrusion is believed more than a simple acute inflammatory response. These "penetration" effects can cause damage to a variety of cells and cellular architecture, causing the appearance of polymorphonuclear neutrophils (PMN) and macrophages as well as the release of IL1, tumor necrosis factor (TNF) and other agents, which can lead to a number of other immunological responses. The soluble stimulatory factors influence the proliferation of lymphocytes and are central to the immune response to vaccines. In addition, these factors influence the migration and activation of resident antigen presenting cells including Langerhan's cells and dendritic cells. The microabrader of the present invention is valuable in promoting significant immune response to a vaccine in the abraded area. The small grooves and furrows created by the microprotrusion array over the abraded area are believed to increase the availability of the vaccine antigen for interaction with antigen-presenting cells compared to a vaccine applied topically in the absence of abrasion or administered using standard needles.

The primary barrier properties of the skin including the resistance to delivery of drugs, vaccines and gene therapeutic agents reside in the outermost layer of the epidermis, referred to as the stratum corneum. The inner layers of the epidermis generally include three layers, commonly identified as the stratum granulosum, the stratum malpighii, and the stratum germinativum. Although not intending to be bound by a particular mechanism of action, it is theorized that once certain drugs or other substances appear below the stratum corneum, there is little resistance for diffusion into subsequent layers of the skin and eventual uptake by cells or absorption by the body through the bloodstream or lymphatic drainage.

Helping a substance to pass through the stratum corneum can be an effective method for facilitating absorption of some substances, and particularly some vaccines, by the body. The present invention is primarily directed to a device and method for facilitating delivery of a substance, and particularly a bioactive substance or pharmaceutical agent, into or through the stratum corneum for more rapid absorption of larger quantities of the bioactive substance or pharmaceutical agent by the patient.

In certain applications of the invention, the microabrader device of the invention penetrates, but does not pierce, the stratum corneum. The substance to be administered using the methods of this invention may be applied to the skin prior to abrading, simultaneous with abrading, or post-abrading. According to one aspect of the methods of the invention, however, certain or specific bioactive substances, including nucleic acids, allergens and live viral vaccines are applied to the skin prior to or simultaneously with abrasion rather than being applied to previously abraded skin. It is believed that delivery of certain substances, such as nucleic acids, allergens and live viral vaccines are improved when such substances are abraded into the skin rather than being passively applied to skin, which has been previously abraded. In another aspect of the method of the invention, however, certain or specific bioactive substances, including virus-like particles and subunit proteins, are believed to have improved delivery when such substances are applied to pre-abraded skin. In other aspects of the method of the invention, however, certain or specific bioactive substances, including whole inactivated or killed viruses, are believed to display similar efficacy whether applied to skin following abrasion or simultaneously with abrasion.

The substance may be delivered into the skin in any pharmaceutically acceptable form. In one aspect of the invention, the substance is applied to the skin and an abrading device is then moved or rubbed reciprocally over the skin and the substance. It is desirable that the minimum amount of abrasion to produce the desired result be used. Determination of the appropriate amount of abrasion for a selected substance is within the ordinary skill in the art. In another aspect of the invention, the substance may be applied in dry form to the abrading surface of the delivery device prior to application. In this embodiment, a reconstituting liquid is applied to the skin at the delivery site and the substance-coated abrading device is applied to the skin at the site of the reconstituting liquid. It is then moved or rubbed reciprocally over the skin so that the substance becomes dissolved in the reconstituting liquid on the surface of the skin and is delivered simultaneously with abrasion. Alternatively, a reconstituting liquid may be contained in the abrading device and released to dissolve the substance as the device is applied to the skin for abrasion. It has been found that certain substances, such as nucleic acid preparations, may also be coated on the abrading device in the form of a gel.

Any device known in the art for disruption of the stratum corneum by abrasion can be used in certain methods of the invention, this includes devices which may pierce the stratum corneum and beyond. These include for example, microelectromechanical (MEMS) devices with arrays of short microneedles or microprotrusions, sandpaper-like devices, scrapers and the like. If the abrading device does not include a reservoir for containment and discharge of fluids from the device, the substance-containing liquid or the reconstituting liquid must be separately applied to the skin prior to or after abrading, for example from a separate dispenser or pump. However, reservoirs may be an integral part of the abrading device. It would be desirable to have the reservoir in fluid communication with the abrading surface of the device or skin, for example: via channels through the needles or protrusions, or via channels which exit the reservoir between such needles or protrusions, or via porous materials, or adjacent to the abrading surface. In this embodiment, the substance or reconstituting liquid is contained in the reservoir of the abrading device and is dispensed to the skin surface prior to abrasion, simultaneously with abrasion, or after abrasion. The abrading device may also include means for controlling the rate of delivery of the substance or reconstituting liquid, or for controlling the amount of substance or reconstituting liquid delivered. As an alternative, a patch, either dry or pre-moistened, may be applied to the site subsequent to abrasion to facilitate reconstitution, or enhance introduction or uptake of substances into the skin. In another aspect of the invention, the patch may contain the medicament and may be applied to skin that was pre-treated with a microabrader device.

Nucleic acids for use in the methods of the invention may be RNA or DNA. A nucleic acid may be in any physical form suitable for topical administration and for uptake and expression by cells. It may be contained in a viral vector, liposome, particle, microparticle, nanoparticle, or other suitable formulation as is known in the art, or it may be delivered as a free polynucleotide such as a plasmid as is known in the art. The nucleic acid will typically be formulated in a pharmaceutically acceptable formulation such as a fluid or gel which is compatible with the nucleic acid. Pharmaceutically acceptable formulations for use in the invention, including formulations for vaccines and allergen compositions, are also well known in the art.

It has been found that minimal abrasion (as little as one pass over the skin) is sufficient to produce an improvement in nucleic acid delivery to skin cells. The amount of nucleic acid delivery and expression continues to increase with increasing numbers of abrasive passes over the skin. Six abrasive passes or more gave the maximum improvement in nucleic acid delivery in experimental animal studies. Although all abrasive passes over the skin may be in the same direction, it is preferred that the direction be altered during abrasion. The most commonly used protocol for delivery of nucleic acid vaccines today is IM injection, usually with additional response enhancers when the dose is low. Determination of the appropriate dose of nucleic acid vaccine to be delivered using the methods of the invention is within the ordinary skill in the art. However, it is an advantage of certain inventive methods that delivery of nucleic acid vaccines is more efficient than IM delivery even without response enhancers, as evidenced by levels of gene expression and stimulation of an immune response.

Amino acids, amino acid derivatives, peptides and polypeptides, particularly allergens and live, attenuated viruses, may also be delivered topically according to the device and methods of the invention. Allergens are conventionally delivered into the skin by intracutaneous puncture using devices similar to the tuberculin tine test. However, it has been unexpectedly found that an enhanced allergenic response can be obtained by simultaneous abrasion and delivery. This produces a more sensitive test and has the advantage that a minor or imperceptible response to the conventional allergen test may be more easily detected using the methods of the invention. Thus, the devices and methods of the invention result in better performance and less skin irritation and erythyma than methods using tine-based devices previously known in the art. Other suitable abraders for delivery of vaccines as well as other medicaments include those disclosed in U.S. application Ser. No. 09/405,488, filed Sep. 24, 1999, and U.S. application Ser. No. 09/576,643, filed May 22, 2000, both herein incorporated by reference, in their entirety. It will be appreciated that the size and shape of the surface area of the abrader, and the shape and pattern of the needles or protrusions can vary according to the particular vaccine or other agent to be delivered and other factors such as ease of application and efficacy, as will be appreciated by those of skill in the art.

Typically, to administer vaccine or other medicament using the certain methods of the present invention, a practitioner will remove the appropriate volume from a vial sealed with a septa using a syringe, and apply the vaccine or medicament to the skin either before or following abrasion using the microabrader. This procedure will at a minimum result in the use of both a syringe needle and a microabrader for each administration procedure, and require time and attention for dosage measurement. Thus, it would be desirable to provide for a kit including the microabrader device either in combination with or adapted to integrate therewith, the substance to be delivered.

The application of minimally invasive, microabrader devices for the delivery of drugs and vaccines clearly present an immediate need for coupling the device with the formulation to provide safe, efficacious, economic and consistent means for administering formulations for enabling immunogenic or other therapeutic responses. The kit provided in accord with one aspect of the invention comprises at least one microabrader delivery device having an abrading surface, which may include microprotrusions projecting from the abrading surface. The microabrader delivery device contained in the kit may be fully integrated, i.e. include a facet adapted to receive or integral with said abrading surface, a handle attachment facet, and a handle that is integral with or detachable from said base. A reservoir containing a vaccine or other medicament, and means to effect delivery may also be integrated into the delivery device. Alternatively, the kit may contain only parts of the microabrader that may be considered disposable (for example, the abrading surface and medicament doses), with reusable items such as the handle and facet being separately supplied. Such kits may, for example, comprise multiple attachable abrading surfaces and multiple vaccine dosages suitable for mass inoculations, with handles and facets being supplied separately (optionally in smaller numbers). Alternatively, the kit may contain one or more complete "one use" microabrader devices that include the abrading surface, facet, handle in "use and dispose" form. In one aspect of the invention, the kit also contains means for containing, measuring, and/or delivering a dosage of a vaccine or other medicament. In another aspect of the invention, the kit also contains an effective dosage of a vaccine or other medicament, optionally contained in a reservoir that is an integral part of, or is capable of being functionally attached to, the delivery device. In another aspect of the invention, the kit also contains a covering that is an integral part of, or is capable of being functionally attached to, the delivery device. Alternatively, the vaccine or other medicament may be supplied in a patch that is packaged in a kit also comprising an abrasion device. In this embodiment, the abrasion device is first used to treat the skin, after which the patch is applied to the treated skin site.

In another aspect of the invention, the kit of the invention comprises a microabrader coated with an effective amount of the medicament or vaccine to be administered. By an "effective amount" or "effective dosage" of a substance is intended to mean an amount that will elicit a desired response in a subject, including, but not limited to, an immunostimulatory response in the case of an allergen or vaccine, or other therapeutic or diagnostic response.

To use a kit as envisioned by certain aspects of the instant invention the practitioner would break a hermetic seal to provide access to the microabrader device and optionally, the vaccine or immunogenic or therapeutic composition. The composition may be preloaded into a reservoir contained in the microabrader device or a separate application device in any suitable form, including but not limited to gel, paste, oil, emulsion, particle, nanoparticle, microparticle, suspension or liquid, or coated on the microabrader device in a suitable dosage. The composition may be separately packaged within the kit package, for example, in a reservoir, vial, tube, blister, pouch, patch or the like. One or more of the constituents of the formulation may be lyophilized, freeze-dried, spray freeze-dried, or in any other reconstitutable form. Various reconstitution media, cleansing or disinfective agents, or topical steriliants (alcohol wipes, iodine) can further be provided if desired. The practitioner would then apply the formulation to the skin of the patient either before or following the abrasion step, or in the case of a preloaded or precoated microabrader device, carry out the abrasion step without separate application of the medicament.

In one aspect of the invention, the closing patch is formed with three components. The first component is skin template. The skin template is a flexible film, typically made from a plastic material, with a skin compatible adhesive layer designed to stick on the skin surface on the distal surface of the skin template. The skin template may include a central opening, which is pre-cut to correspond to the desired abrasion area of the skin. The opening may also be at an edge of the skin template. The size of the opening corresponds to the area of the skin surface to be abraded. In one aspect of the invention, the opening geometry is correlated to the precise area to be abraded; wherein the area is determined clinically from previously conducted studies on the relationship of abraded area and delivery of an effective amount of drug or vaccine. Selection of the opening size to correspond to a predetermined area allows a clinician to readily observe the area of skin that must be abraded for effective delivery. The opening may be any shape but is typically rectangular. In an alternate embodiment the opening is a slot shaped opening. Although not critical for the invention, the skin template is typically placed onto the skin of the patient prior to the abrasion, and is affixed to the skin by a skin compatible adhesive. The skin template may be printed with indicia to indicate directions for use, or for proper placement locations of subsequent coverings. The skin template assists skin pre-treatment before vaccine or drug delivery by exposing to the skin abrader the predetermined skin surface area. Skin abrasion is performed through the opening of the skin template. The second component of this embodiment of the invention is an opening cover. Typically, the opening cover is formed from a pliable plastic material. Alternatively, the opening cover may be formed from a semi-rigid material to form a closed chamber when covering the window of the skin template. This closed chamber acts to substantially contain the delivered volume of drug/vaccine/substance. Forming the opening cover in the general shape of a dome may further enlarge the volume of the closed chamber, thus adding to the volume of substance that may be delivered to the abraded area of skin.

It is desirable that the distal surface of the opening cover, which contacts the abraded area of the skin, should prevent absorption of drug (or vaccine) and/or adhesion of the skin to the to the opening cover. In order to achieve this non-binding state, the surface properties of the opening cover may be selected or treated such that they are highly hydrophobic, at least on the distal surface. Other surface treatments and/or materials to prevent binding are well known in the art and could be used for the distal skin contact area of the opening cover. Alternatively, the distal surface of the opening cover may be coated with a releasable drug/vaccine formulation, which is then absorbed by the abraded area upon contact with the abraded area. For example, the distal surface of the opening cover may be coated with hydrogel matrix or other polymeric matrix, or as micro or nano particles coated on the distal surface.

The third component of this embodiment of the invention is a dressing cover which is typically formed of a flexible plastic film with at least a distal adhesive layer designed to stick both on the back of the opening cover and the skin template. The dressing cover is used after the abrasion/delivery process is completed. Alternatively, the dressing cover does not adhere to the opening cover and only serves to contain the opening cover between the skin template and the dressing cover. Alternatively, the dressing cover has an opening cover integrally formed onto the distal surface of the dressing cover. Thus, in this embodiment of the invention, the clinician is provided both a template for the abrasion process and a dressing to dress the abraded area after the abrasion. Alternatively, the skin template is not adhered to the skin but is only used as a temporary guide for placement of indicia, which is printed directly onto the patient's skin. Alternatively, the indicia are printed directly onto the patient's skin without the use of a skin template. In each of the aforementioned embodiments, the indicia on the patient's skin indicate the size of the abraded area.

Figure 1A:
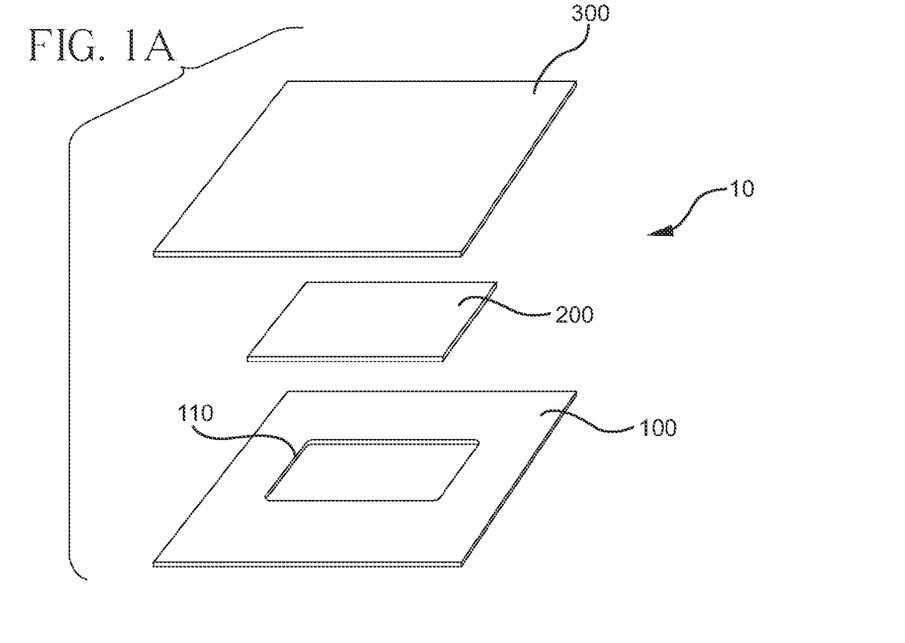
FIG. 1A and FIG. 1B are a schematic perspective view of an apparatus for covering an abraded portion of skin of the invention.
Figure 1B:
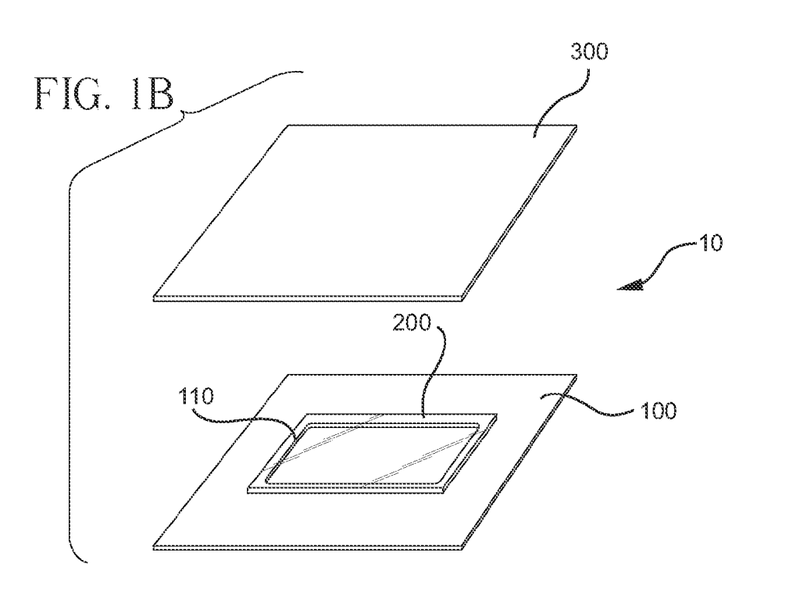
Figure 2:
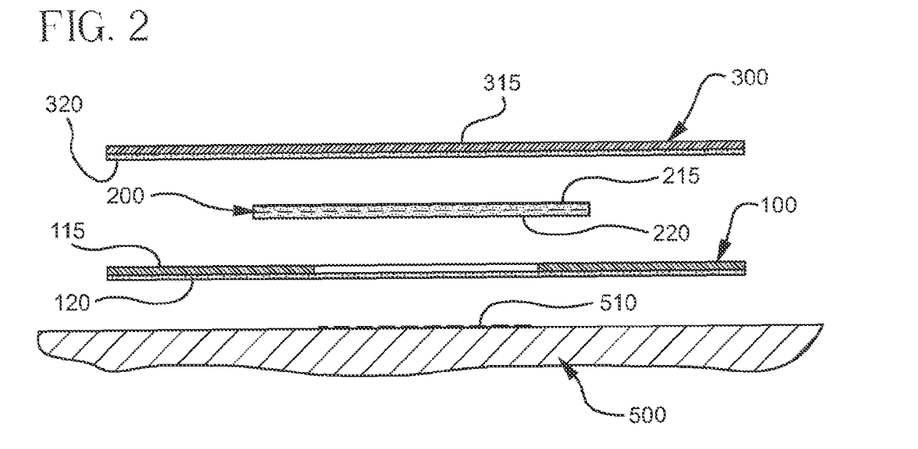
FIG. 2 is a schematic cross section of the apparatus of FIG. 1A.

Now referring to FIG. 1A, FIG. 1B and FIG. 2, shown is a patch 10 of the invention with a skin template 100, constructed of a flexible material, having a central opening 110. Central opening 110 is sized to be slightly larger than the pre-determined abrasion area 510. Skin template 100 has proximal surface 115 and distal surface 120. Distal surface 120 may be coated with a skin compatible adhesive. It is desirable to construct skin template 100 from a clear or translucent material. Skin template 100 is placed onto the skin 500 with central opening 100 over the desired abrasion area. Preferably, skin template 100 conforms to the skin 500 to which it is applied. Proximal surface 115 may contain indicia with directions for use of the abrasion process, or for proper placement location of subsequent coverings. After skin template 100 has been adhered to the skin 500, a microabrader is engaged to the skin 500 for abrasion through central opening 110. After the abrasion process is complete, cover 200 is placed over opening 110. Preferably, cover 200 is sized to be slightly larger than opening 110. Cover 200 may be constructed of a clear or translucent material. As stated previously, distal surface 220 of cover 200 is, or at least the periphery of distal surface 220 of cover 200 may be coated with adhesive so that the periphery of distal surface 220 adheres to proximal surface 115 of skin template 100. Cover 200 also has proximal surface 215. Cover 200 and skin template 100 are covered by dressing 300. Dressing 300 also has distal surface 320. Distal surface 320 is preferably covered with adhesive, which may bond to both cover 200 and skin template 100, although distal surface 320 may only bond to skin template 100 and trap cover 200 therebetween. Proximal surface 215 of cover 200 may also be bonded to dressing 300 so that they are a single unit. It is desirable that dressing 300 is constructed of a clear or translucent material.

Figure 3:
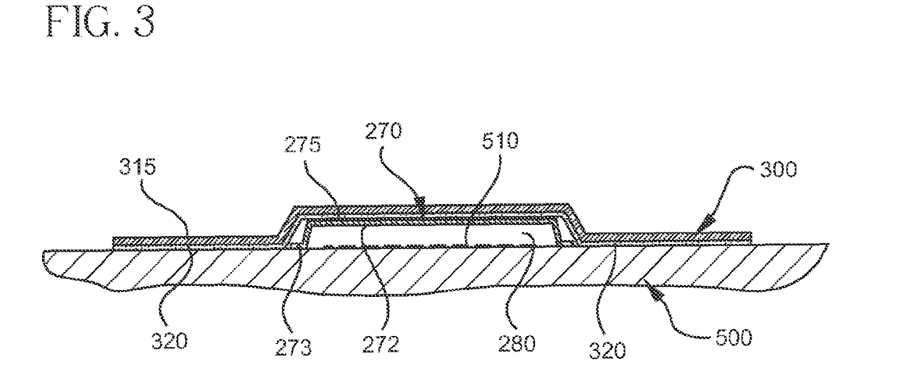
FIG. 3 is a schematic cross section of an alternate embodiment of the invention, in the same view as FIG. 2.

Now referring to FIG. 3, which shows another aspect of the invention, dressing cover 300 is used in conjunction with a semi-rigid dome 270. The dome 270 serves to cover the abraded area 510 of the skin 500 and prevent adhesion of the skin. The dome 270 is sized such that a chamber 280 is formed between the distal surface 272 of the dome 270 and the skin 500, when the patch 10 is applied. Proximal surface 275 of the dome 270 may be adhered to the dressing cover 300. The material of the dome 270 is a semi-rigid plastic, aluminum, other semi-pliable metal or metal film, or any other material compatible with the formulated active ingredient. The offset of the distal surface 272 of the chamber 280 from the skin 500, when the patch 10 is applied is approximately 0.1 to 0.5 mm and the length and width of the chamber is slightly larger than the abraded area 510. In one aspect of the invention the chamber 270 is empty and provides a closure of the abraded/treated skin surface. The chamber 270 protects the abraded area 510 by the cushion of empty space. The dressing cover 300 is designed to cover the abraded area 510 of skin 500 after skin abrasion and application of drug or vaccine.

Figure 4:
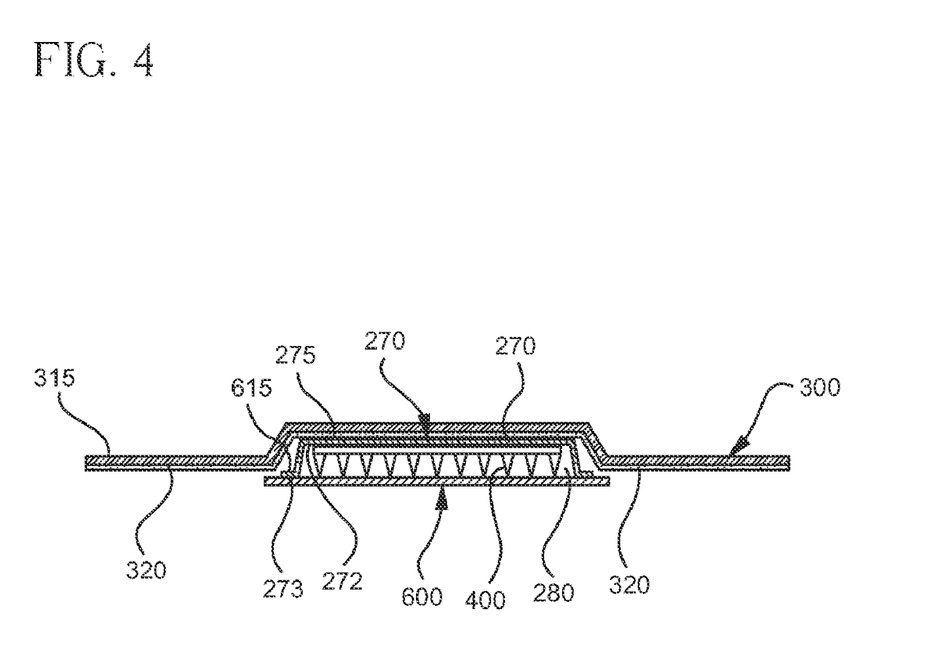
FIG. 4 is a schematic cross section of an alternated embodiment of the invention in the same view as FIG. 2.

Now referring to FIG. 4, an alternate embodiment, chamber 280 contains a drug or vaccine formulation, which is the same as the drug or vaccine delivered by the abrasion process. Alternatively the chamber 280 contains second drug, vaccine or other bioactive substance, which enhances delivery of the first drug or vaccine. For example, the second substance may be an adjuvant or immune-stimulant that enhances delivery of the vaccine or vaccine antigen. Alternatively, a skin abrader 400 formed by a needle array is integrated into the chamber 280. The chamber is pre-filled with the drug or vaccine and sealed with a closure 600 ensuring drug/device integrity and sterility.

Figure 5:
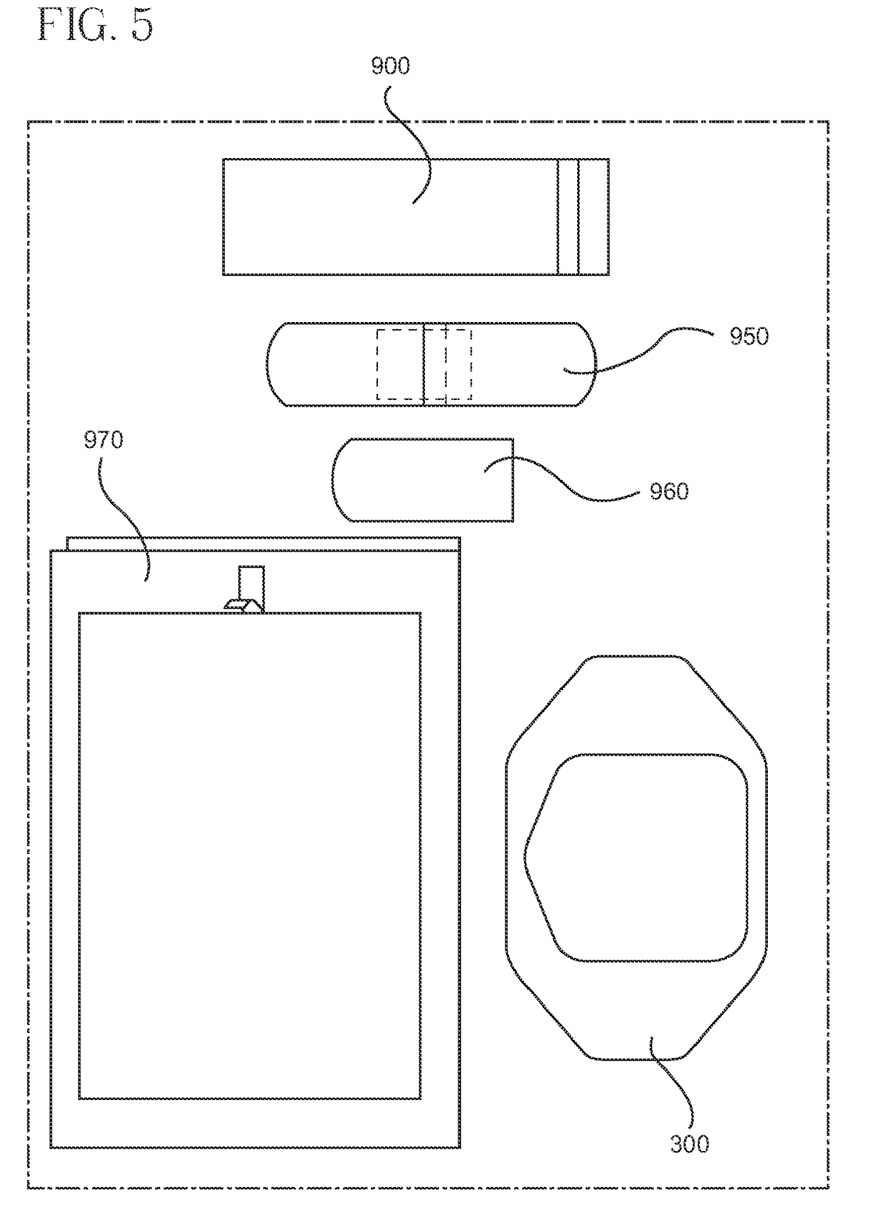
FIG. 5 is a top view of kit of the invention.

Now referring to FIG. 5, which shows a kit of the invention. Shown are dressing 300 with its primary packaging 970, which ensures the sterility of dressing 300. Cover 960 is used to cover the abraded area. For example, an expedient cover 960 may be composed of the sterile backing of a standard sterile adhesive bandage 950. Shown is the primary packaging 900 for the sterile, adhesive bandage 950 with cover 960.

Figure 6:
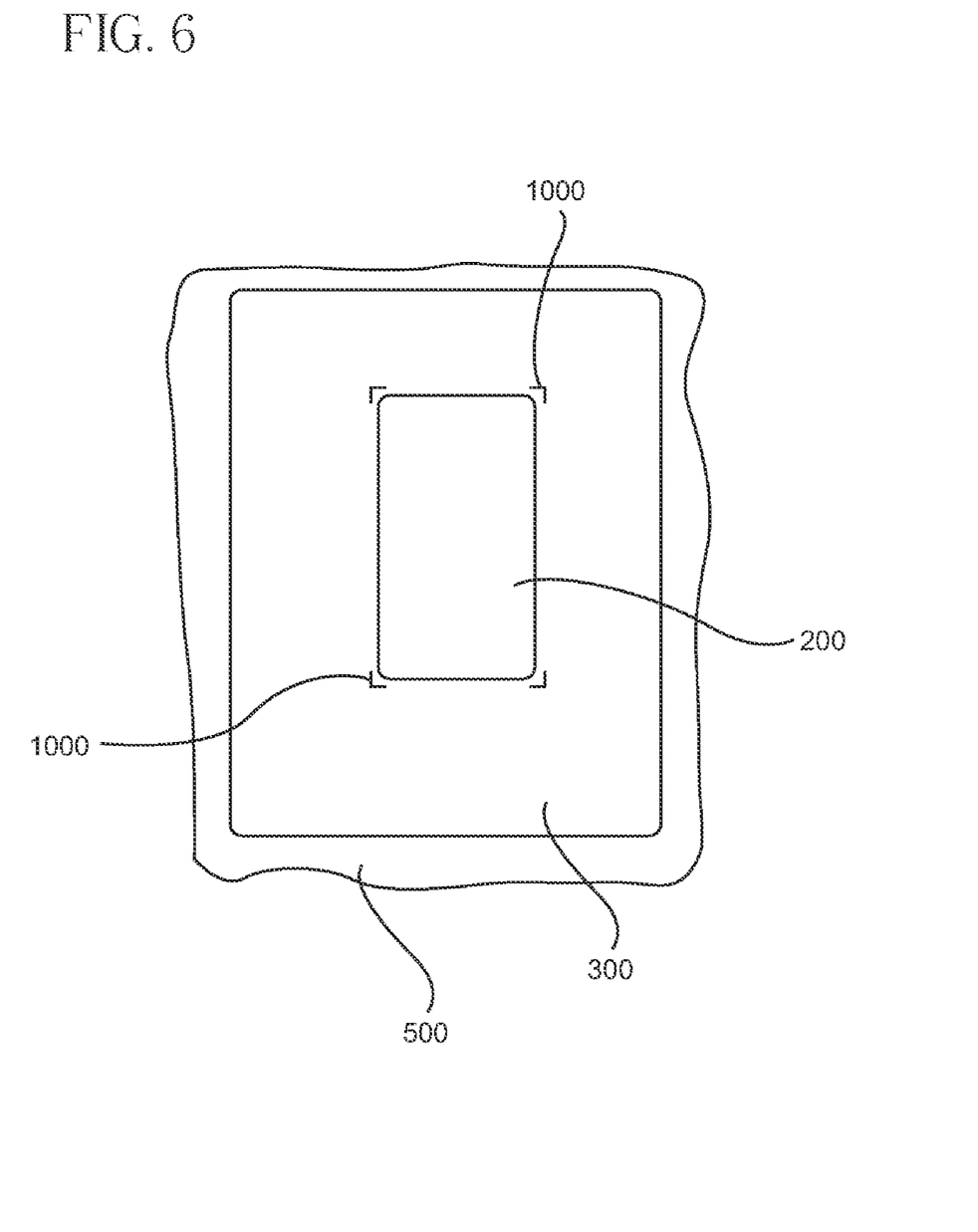
FIG. 6 is a top view of a patient's skin with an apparatus according to one embodiment the invention applied to the skin.

Now referring to FIG. 6, which shows an alternate embodiment of the invention without a skin template, adhered to the skin. In this embodiment, skin template 100 (not shown) is temporarily placed against skin 500 and indicia 1000 is marked directly onto the skin. The skin template is only used as a temporary guide for placement of indicia 1000, which is printed directly onto the patient's skin. Alternatively, the indicia are printed directly onto the patient's skin without the use of a skin template. The indicia 1000 on the patient's skin indicate the size of the pre-selected abraded area or for proper placement locations of subsequent coverings. In this figure, cover 200 is placed directly onto the skin and protects abraded area 510. Then dressing 300 is place onto cover 200 and the skin.

Figure 7A:
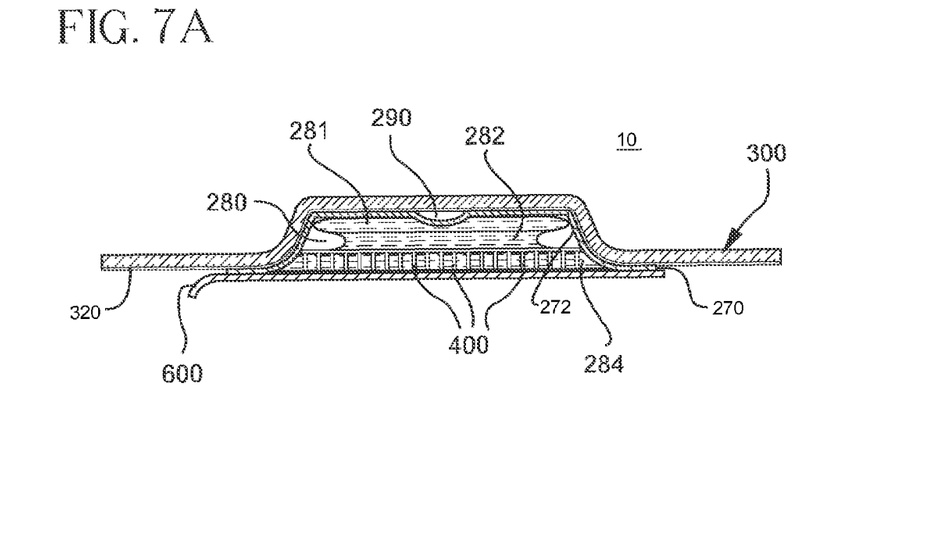
FIG. 7A and FIG. 7B are a schematic cross sectional view of an alternate embodiment of the invention.
Figure 7B:
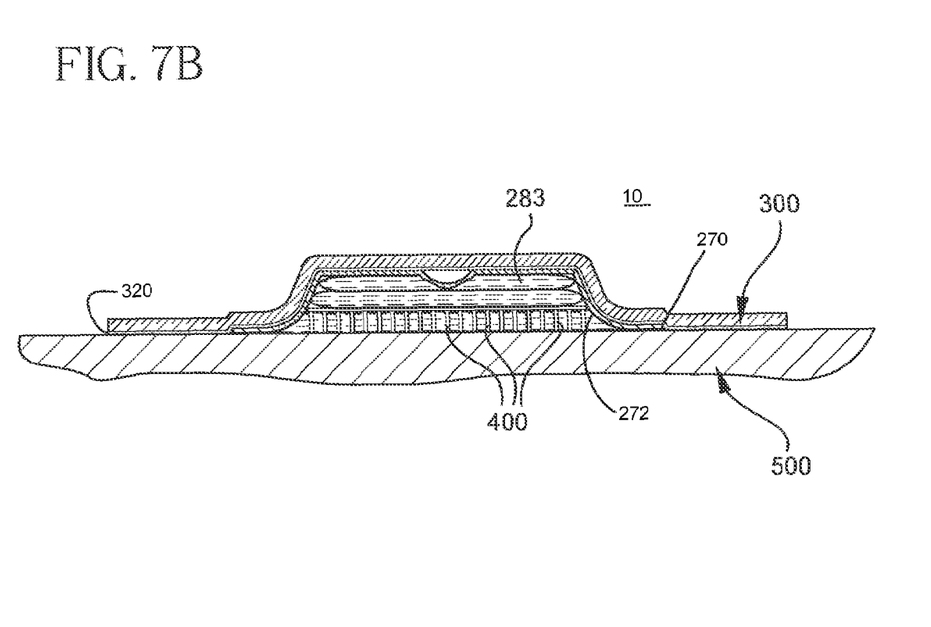

Now referring to FIG. 7A and FIG. 7B, which show another embodiment of the invention. In this embodiment, patch 10 is both a primary packaging for a drug or vaccine, and delivery system to penetrate the skin after skin disruption and also a closing patch. The primary packaging is pre-fillable with drug or vaccine formulation based on liquid or gel formulation. The drug delivery system is based on two integrated features: a dressing cover 300, which is applied to the skin surface after abrasion by an abrader, and a secondary delivery system. In this embodiment, the dressing cover 300 is designed with a distal surface 320 which has an adhesive designed to stick onto the skin surface. The secondary delivery feature is housed in chamber 280. Chamber 280 is bounded by the distal surface 272 of dome 270, and closure 600. The periphery 273 of the distal portion of the chamber 280 is substantially planer, in order to provide a surface for closure 600 to be attached. The dressing 300 supporting the adhesive exhibits some elasticity property to ensure a firm contact of dome 270 onto the skin surface. Before applying the dressing cover 300 to the skin surface, closure 600 is removed exposing the chamber 280. The open chamber 280 is applied to the skin with the dressing cover 300 so that the chamber 280 is closed, now bounded by the dome 270 and the skin surface 500.

The chamber comprises three compartments: the drug reservoir 284, the swellable reservoir 282, and the aqueous reservoir 281. The drug reservoir 284 is filled with the drug to be delivered, which may be in the form of a powder, liquid, or gel. The distal portion of the drug reservoir 284 optionally contains a microneedle array. The swellable reservoir 282 is filled with a first material, which expands in contact with water. Typically the swellable reservoir 282 is filled with a dry polymer. Many swellable materials are known in the art, such as a Dextran powder, however, any synthetic polymer actuated by humidity can be potential candidate and could be used in the swellable reservoir 282. The aqueous reservoir 281 contains a second material, which, when introduced to the first material, causes an expansion in one or both materials. Typically, the aqueous reservoir 281 is filled with water. As the co-mingled materials expand, the drug in the drug reservoir 284 is forced into the skin since the chamber is formed by the boundary of a semi-rigid, non-permeable dome 270 and permeable skin 500. Optionally, the microneedle array 400 is also forced into the skin by the expansion of the co-mingled first and second materials. Each of the three compartments, as well as the dome and the closure could be constructed from aluminum, since aluminum is an approved material as primary drug packaging; however, any suitable medical grade material can be used. Co-mingling of the first and seconds substances is accomplished by activation of a piercing element 290 in the form of a spike or a sharp point. To activate the device, a patient or clinician applies pressure upon the proximal portion of the dome causing piercing element 290 to rupture aqueous reservoir 281 and allow co-mingling of the first and second substances within chamber 280, causing them to expand and force the drug into the skin.

In this embodiment, the use of the device is outlined in the following steps: prepare the skin surface by disinfecting and/or pre-treating with a microabrader; expose the adhesive on the dressing cover; remove the closure; adhere the patch to the skin surface; activate the device, wherein the first and second material are co-mingled and start to expand; allow patch to remain on the skin for the required period of drug delivery; remove the patch.

During the period of drug delivery, the drug is in direct contact with the skin surface like a topical application, and as soon as the patch is activated, the first material co-mingles with the second material and the expansion of the two materials moves the drug toward the skin surface. Optionally, the expansion also moves the microneedle array toward the skin surface so that the microneedle array disrupts the stratum corneum.

What is claimed is:

1. A method for delivering a substance into skin comprising the steps of:
    applying printed indicia onto the skin which corresponds to a predetermined abrasion area,
    providing an abrader having an abrading surface with an abrading surface area said abrader surface area having a plurality of microprotrusions;
    moving the abrader across said skin to produce an abraded area within the bounds of said pre-determined abrasion area thereby producing abrasions in the skin within said predetermined abrasion area, and;
    applying said substance to the abraded area.

2. The method of claim 1 further comprising covering said abrasion area with a cover after said abrader is moved across said skin.

3. The method of claim 2 wherein said cover is coated with a drug.

4. The method of claim 2 wherein said cover is coated with a vaccine.

5. The method of claim 1 further comprising providing a skin template; wherein said template is adapted for removable conforming engagement to intact skin and the skin template provides guidance for marking the indicia directly onto the skin.

6. The method of claim 1 wherein said substance is applied prior to abrasion.

7. The method of claim 1 wherein said substance is applied during abrasion.

8. The method of claim 1 wherein said substance is applied following abrasion.

9. The method of claim 1 wherein said microprotrusions are at least partially coated with said substance to be delivered.

10. The method of claim 1 wherein said indicia further comprises a plurality of corner marks outlining the predetermined abrasion area.

11. A system for delivering a substance into skin comprising:

a skin marker, for marking printed indicia directly onto the skin;

a skin template, which is applied to the skin and has an opening corresponding to a predetermined abrasion area, wherein the skin template is used as a guide for the skin marker to form the indicia which correspond to the predetermined abrasion area, and an abrader having an abrasion surface containing a plurality of frustoconical or frustopyramidal microprotrusions further comprising at least one scraping edge projecting from said abrading surface adapted for movement across said skin to produce an abraded area on the skin within the bounds of said predetermined abrasion area.

12. The system of claim 11 further comprising a cover wherein said cover contacts at least a portion of said abrasion area.

13. The system of claim 12 wherein said cover is coated a substance selected from the group consisting of drug, vaccine, and bioactive substance.

14. The system of claim 12 wherein said cover is coated with a releasable retention means for retaining a substance selected from the group consisting of drug, vaccine, and bioactive substance.

15. The system of claim 11 wherein said substance is applied to the predetermined abrasion area.

16. The system of claim 15 wherein said substance is applied prior to abrasion.

17. The system of claim 15 wherein said substance is applied during abrasion.

18. The system of claim 15 wherein said substance is applied following abrasion.

19. The system of claim 15 wherein said microprotrusions are at least partially coated with said substance to be delivered.

20. The system of claim 11 wherein said indicia further comprises a plurality of corner marks outlining the predetermined abrasion area.

\* \* \* \* \*